United States Patent [19]

Darsow

[11] Patent Number: 5,639,917
[45] Date of Patent: Jun. 17, 1997

[54] PROCESS FOR PREPARING 1-(4-CHLOROPHENYL)-4,4-DIMETHYL-PENTAN-3-ONE

[75] Inventor: Gerhard Darsow, Krefeld, Germany

[73] Assignee: Bayer Aktiengesellschaft, Leverkusen, Germany

[21] Appl. No.: 601,913

[22] Filed: Feb. 15, 1996

[30] Foreign Application Priority Data

Feb. 21, 1995 [DE] Germany .................. 195 05 938.7

[51] Int. Cl.$^6$ ........................................ C07C 45/62
[52] U.S. Cl. ................................. 568/316; 568/318
[58] Field of Search .............................. 568/318, 316

[56] References Cited

U.S. PATENT DOCUMENTS

| | | | |
|---|---|---|---|
| 3,912,752 | 10/1975 | Meiser et al. | 260/308 |
| 4,020,108 | 4/1977 | Ehmann | 568/318 |
| 4,041,083 | 8/1977 | Gradeff et al. | 568/318 |
| 4,205,075 | 5/1980 | Baldwin et al. | 424/269 |
| 4,243,405 | 1/1981 | Balasubramanyan et al. | 71/76 |
| 4,260,829 | 4/1981 | Horner et al. | 568/318 |
| 4,284,639 | 8/1981 | Krämer et al. | 424/269 |
| 4,921,529 | 5/1990 | Lantzsch et al. | 71/92 |
| 4,940,819 | 7/1990 | Kiel et al. | 568/318 |

FOREIGN PATENT DOCUMENTS

| | | | |
|---|---|---|---|
| 0040345 | 11/1981 | European Pat. Off. | 71/76 |
| 0354991 | 2/1990 | European Pat. Off. | 568/318 |
| 1478704 | 7/1967 | France . | |
| 2201063 | 7/1973 | Germany | 424/269 |
| 2737489 | 2/1978 | Germany | 71/76 |
| 2705678 | 8/1978 | Germany | 424/269 |
| 3702301 | 9/1987 | Germany . | |
| 4004031 | 10/1990 | Germany . | |

OTHER PUBLICATIONS

J.S. Gillespie, Jr. et al., Tetrahedron, vol. 31, pp. 3–8, (1975).

Chemical Abstracts, vol. 84, abstract No. 73906u, p. 415, abstract of FR 2,253,505, (1976).

*Primary Examiner*—James H. Reamer
*Attorney, Agent, or Firm*—Sprung Horn Kramer & Woods

[57] ABSTRACT

There is described a continuous process for preparing 1-(4-chlorophenyl)-4,4-dimethyl-pentan-3-one from 1-(4-chlorophenyl)-4,4-dimethyl-pent-1-en-3-one, wherein the 1-(4-chlorophenyl)-4,4-dimethyl-pent-1-en-3-one is hydrogenated in the liquid phase in alcoholic solution with hydrogen at a pressure of from 50 to 400 bar and a reaction temperature of from 80° to 160° C. over support-free shaped bodies of pressed powders of the elements of the iron subgroup of transition group VIII of the Periodic Table or their alloys or mixtures with one another or their alloys or mixtures with elements of transition group VI, which shaped bodies are arranged in a fixed bed, to give 1-(4-chlorophenyl)-4,4-dimethyl-pentan-3-one. The shaped bodies have a compressive strength of from 20 to 250N and an internal surface area of from 10 to 80 m$^2$/g.

14 Claims, No Drawings

PROCESS FOR PREPARING 1-(4-CHLOROPHENYL)-4,4-DIMETHYL-PENTAN-3-ONE

The present invention relates to a new low-cost, continuously operating process for preparing 1-(4-chlorophenyl)-4,4-dimethyl-pentan-3-one, in which only very small amounts of the materials 1-(4-chlorophenyl)-4,4-dimethyl-pentan-3-ol and 1-phenyl-4,4-dimethyl-pentan-3-one usually arising as by-products in the hydrogenation of 1-(4-chlorophenyl)-4,4-dimethyl-pent-1-en-3-one are formed.

1-(4-Chlorophenyl)-4,4-dimethyl-pentan-3-one is an important starting material for the preparation of 1-(4-chlorophenyl)-3-(1,2,4-triazol-1-yl-methyl)-4,4-dimethyl-pentan-3-ol which has excellent fungicidal and plant growth-regulating properties (EP-A-0 040 345).

It is known that 1-(4-chlorophenyl)-4,4-dimethyl-pentan-3-one can be prepared batchwise by hydrogenation of 1-(4-chlorophenyl)-4,4-dimethyl-pent-1-en-3-one in organic solvents such as methanol, toluene, xylene, cyclohexane, isooctane, ethers or esters over Ni-containing catalysts in powder form (EP-A 0 354 991).

It is also known that 1-(4-chlorophenyl)-4,4-dimethyl-pentan-3-one can be prepared batchwise by hydrogenation of 1-(4-chlorophenyl)-4,4-dimethyl-pent-1-en-3-one over Ni in powder form, the reaction being carried out in the presence of toluene or xylene as solvent (German Offenlegungsschrift 4 004 03 1); the starting material is prepared, for example, by condensation of 4-chloro-benzaldehyde with 3,3-dimethyl-butan-2-one.

The present invention provides an ecologically and technically advantageous continuous process for preparing 1-(4-chlorophenyl)-4,4-dimethyl-pentan-3-one from 1-(4-chlorophenyl)-4,4-dimethyl-pent-1-en-3-one, wherein 1-(4-chlorophenyl)-4,4-dimethyl-pent-1-en-3-one is hydrogenated in alcoholic solution by a catalysed liquid-phase hydrogenation under a pressure of from 50 to 400 bar at a temperature of from 30° to 70° C. over shaped bodies of pressed powders of the elements of the iron subgroup of transition group VIII of the Periodic Table or their alloys or mixtures with elements of transition group VI, which shaped bodies are arranged in a fixed bed, to give 1-(4-chlorophenyl)-4,4-dimethyl-pentan-3-one.

The course of the reaction is shown by the following reaction scheme:

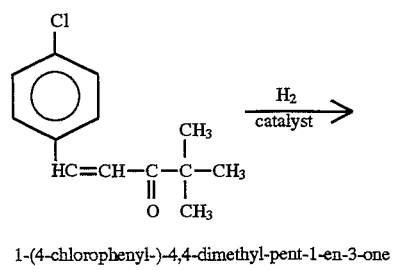

1-(4-chlorophenyl-)-4,4-dimethyl-pent-1-en-3-one

-continued

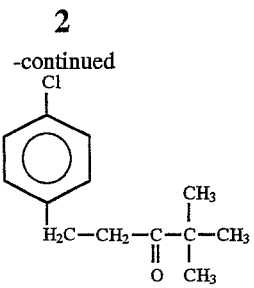

1-(4-chlorophenyl)-4,4-dimethyl-pentan-3-one

In the known processes for preparing 1-(4-chlorophenyl)-4,4-dimethyl-pentan-3-one, use is made of powder suspension processes in which the 1-(4-chlorophenyl)-4,4-dimethyl-pent-1-en-3-one is hydrogenated in a solvent over pulverulent catalysts using hydrogen.

Batchwise processes have the disadvantage that their capacity relative to the reaction volume is very small and there is thus a need for large reaction apparatus and storage tanks. Energy consumption and personnel needs are relatively high.

Continuous powder catalyst processes which use one or more hydrogenation reactors connected in a cascade avoid some of these disadvantages. However, there remains the requirement for measuring in the pulverulent catalysts in a guided manner, pumping them around and quantitatively filtering them off from the reaction product. The catalyst slurry pumps are subject to high mechanical wear. The quantitative removal of the pulverulent catalysts from the reaction product is complicated. In addition, there is a great danger of relatively quickly reducing the catalyst activity by the additional operations. It is therefore desirable, because it is advantageous, to allow the reaction to proceed over fixed-bed catalysts. Such catalysts have to have a high activity which must not fall over a relatively long period of time, because frequent replacement of catalyst is likewise complicated in the case of fixed-bed reactions.

According to the invention, 1-(4-chlorophenyl)-4,4-dimethyl-pent-1-en-3-one, dissolved in alcohols, is continuously hydrogenated to give 1-(4-chlorophenyl)-4,4-dimethyl-pentan-3-one, using as hydrogenation catalysts support-free shaped bodies of pressed metal powders of one or more elements of the iron subgroup of transition group VIII of the Periodic Table, which shaped bodies are arranged in a fixed bed in a reactor. In addition, it can be useful to alloy or mix the metals of the iron subgroup with elements of transition group VI of the Periodic Table which have an activating effect. The powders used can additionally contain certain amounts of non-catalytic elements (e.g. silicon, aluminium, carbon, titanium) without reducing the high activity. The solid bodies have to have a compressive strength of from 20 to 250N on the surface of the shaped body and an internal surface area of from 10 to 80 $m^2/g$.

The 1-(4-chlorophenyl)-4,4-dimethyl-pent-1-en-3-one used has a purity of >99%. However, it is also possible to use distillation runback streams having lower concentrations of 1-(4-chlorophenyl)-4,4-dimethyl-pent-1-en-3-one.

Monoalcohols for the process of the invention are, in particular, those having from 1 to 4 carbon atoms, such as methanol, ethanol, propanol, i-propanol, butanol, i-, sec- and tert-butanol, preferably methanol and ethanol, particularly preferably methanol. Alcohols having more than 4 carbon atoms and diols are suitable in principle as reaction medium but are more expensive and, owing to their boiling point, more difficult to separate from the reaction product. Mixtures of the alcohols specified can likewise be used. 1-(4-Chlorophenyl)-4,4-dimethyl-pent-1-en-3-one is used as a 15 to 20% strength by weight solution in the specified alcohols.

It can here be advantageous to adjust the pH of the solution to from 8 to 10 using small amounts of alkali (NaOH, KOH, $Na_2CO_3$, $K_2CO_3$, etc., in an amount of from 0.1 to 0.2 g/l) and to add a small amount (from 0.1 to 0.2 g/l) of an organic sulphur compound, e.g. bis-(2-hydroxy-ethyl) sulphide, to the solution.

The compressive strength of the support-free shaped bodies can be determined in accordance with DIN 50 106. The testing of support-free shaped bodies for the internal surface areas required and thus for usability for the process of the invention can be carried out by methods which have been described by F. M. Nelsen and F. T. Eggertsen, Analyt. Chem. 30 (1958), pp. 1387–1390 or S. J. Gregg and S. W. Sing, Adsorption, Surface Area and Porosity, London 1982, chapters 2 and 6.

The iron subgroup of transition group VIII of the Periodic Table contains the metals iron, cobalt and nickel. The support-free shaped bodies to be used according to the invention contain (i) one or more of these metals in amounts of at least 60, preferably 70, in particular at least 80, % by weight, based on the support-free shaped bodies. Fe, Co and Ni are here present in any ratios to one another. Preferably, the shaped bodies contain Ni as (i) in an amount of from 60 to 100% by weight, particularly preferably from 80 to 100% by weight, of all metals (i).

Transition group VI of the Periodic Table contains the elements chromium, molybdenum and tungsten. The support-free shaped bodies to be used according to the invention can contain (ii) one or more of these metals. These metals (ii) are present in an amount of from zero to 15% by weight, based on the support-free shaped bodies. Preferably, the shaped bodies contain one or more of these metals in amounts of from 0.1 to 15% by weight, particularly preferably from 0.3 to 10% by weight, very particularly preferably from 0.5 to 5% by weight, based on the support-free shaped bodies.

The support-free shaped bodies to be used according to the invention can additionally contain, in each case based on support-free shaped bodies, (iii) from zero to 25% by weight, preferably from zero to 15% by weight, particularly preferably from zero to 10% by weight, of other elements. Examples of such elements which do not act catalytically include aluminium, silicon, carbon and titanium. According to a particularly preferred embodiment, the support-free shaped bodies contain, in addition to the components (i) and (ii), not more than 8% by weight of aluminium and not more than 5% by weight of other elements.

The support-free shaped bodies can be produced by customary methods by pressing the metal powders on tabletting or pelletizing machines under a high pressure, with it being possible to improve the adhesion of the metal particles by also using graphite in amounts of from 0.5 to 1.5% by weight, based on the total weight of the constituents forming the catalyst, or adhesives in small amounts. The support-free shaped bodies are preferably produced in an oxygen-free atmosphere to avoid surface for the reaction procedure are tableted or pelletized shaped bodies having dimensions of from 2 to 7 mm, preferably from 3 to 5 mm. Of considerable importance is the compressive strength of the shaped bodies which, according to the invention, is from 20 to 250N, preferably from 110 to 220N.

Lower compressive strengths lead to disintegration of the shaped bodies or to erosive removal of material which would cause metallic contamination of the reaction product. Another factor of considerable importance is the internal surface area of the shaped bodies which, according to the invention, is from 10 to 80 $m^2/g$ and is decisive for a very quantitative conversion of the starting materials. Macroscopically, the shaped bodies have a smooth surface.

The hydrogenation process is carried out using pure hydrogen precompressed to a pressure of from 50 to 400 bar, preferably from 100 to 300 bar, using 10-fold to 40-fold molar hydrogen excesses.

The hydrogenation is carried out continuously in a fixed-bed process over the support-free shaped bodies of the type described serving as hydrogenation catalysts, by allowing the 1-(4-chlorophenyl)-4,4-dimethyl-pent-1-en-3-one to be hydrogenated, dissolved in alcohol, to flow either in cocurrent with the previously mixed-in hydrogen from the bottom upwards over the shaped bodies present in the hydrogenation reactor or from the bottom upwards counter to the hydrogen flowing from the top (countercurrent process).

The hydrogenation process is carried out at temperatures from 30° to 160° C., preferably from 40° to 80° C. Lower temperatures require higher residence times or acceptance of incomplete conversion of the 1-(4-chlorophenyl)-4,4-dimethyl-pent-1-en-3-one. Higher temperatures lead to increased formation of by-products. The starting materials are preferably preheated to from 30° to 70° C., particularly preferably from 40° to 60° C., prior to entering into the reactor.

The hourly space velocity over the catalyst can be from 100 to 300 g of 1-(4-chlorophenyl)-4,4-dimethyl-pent-1-en-3-ol/l of catalyst.

The hydrogenation reactor can be either a single high-pressure tube of steel or a steel alloy which is completely or partially filled with the support-free shaped bodies, with the use on trays (wire baskets or the like) also being able to be useful, or else a jacketed high-pressure tube bundle whose individual tubes are completely or partially filled with shaped bodies.

Quite unexpectedly, high catalyst operating lives of 15,000 hours and more can be achieved under the reaction conditions indicated, which leads to catalyst consumptions <0.1% by weight which have hitherto not been achieved in the hydrogenation of 1-(4-chlorophenyl)-4,4-dimethyl-pent-1-en-3-one.

The reaction mixture leaving the hydrogenation reactor comprises, after decompression in which the excess hydrogen can be collected and after compression and replacement of hydrogen consumed can be reused, and after the distillative removal of the solvent, more than 99% by weight of 1-(4-chlorophenyl)-4,4-dimethyl-pentan-3-one at a conversion of starting material of from 99.9 to 100%.

It can contain organic impurities in an amount of up to 0.8% by weight. The 1-(4-chlorophenyl)-4,4-dimethyl-pentan-3-one can be obtained in a purity of $\geq 99.9\%$ by weight after distillative removal of the impurities, and in this purity can be used for all further processes.

EXAMPLES

Example 1

A vertical, thermally insulated high-pressure tube of stainless steel having an internal diameter of 45 mm and a length of 1 m was filled with 1.4 l of a hydrogenation catalyst produced by tableting of nickel powder, this catalyst having, at a cylinder height of 3 mm and a diameter of 3 mm, a compressive strength of 147N on the cylindrical surface and an internal surface area of 63 $m^2/g$. 1400 ml/h of an 18% strength by weight solution of 1-(4-chlorophenyl)-4,4-dimethyl-pent-1-en-3-one having a purity of >99% by weight in pure methanol, the solution additionally containing 0.2% by weight of NaOH and 0.2% by weight of bis-(2-hydroxy-ethyl)sulphide, were, together with the 20-fold molar amount of high-purity hydrogen under a pressure of 300 bar, pumped continuously through this tube, namely from the bottom upwards.

Solution to be hydrogenated and hydrogen were previously passed together through a heat exchanger and heated sufficiently for them to enter the high-pressure tube at a temperature of 55° C. The mixture of liquid reaction product and excess hydrogen leaving the high-pressure tube was passed to a separator from where the hydrogen, after addition of the amount consumed, was again pumped together with new solution to be hydrogenated into the preheater and from there again into the high pressure tube.

After hydrogenation and distillative removal of the solvent, the reaction product was analysed by gas chromatography. It contained 0.35% by weight of 1-(4-chlorophenyl)-4,4-dimethyl-pentan-3-ol and 0.04% by weight of 1-phenyl-4,4-dimethyl-pentan-3-one. The content of 1-(4-chlorophenyl)-4,4-dimethyl-pentan-3-one was 99.21% by weight (remainder to 100%=starting material and unknown by-products).

After the distillative removal of the impurities, the 1-(4-chlorophenyl)-4,4-dimethyl-pentan-3-one isolated had a purity of 99.9% by weight.

After a running time of 5400 hours, the catalyst had an unchanged activity so that the composition of the reaction product did not change over this period of time.

Example 2

At a temperature of 60° C. and hydrogen pressure of 200 bar in a high-pressure tube as in Example 1, the hydrogen was passed, in a reversal of the reaction flow of Example 1, in countercurrent to the upwards flowing solution to be hydrogenated with the same amount per hour as in Example 1 being hydrogenated. The catalyst had been obtained by tableting a pulverized nickel-iron alloy. The alloy contained 15% by weight of iron in nickel. The tablets had, at a cylinder height of 5 mm and a diameter of 5 mm, a compressive strength of 137N on the cylindrical surface and an internal surface area of 74 m²/g.

After a running time of 2400 hours, the conversion of the 1-(4-chlorophenyl)-4,4-dimethyl-pent-1-en-3-one used was 99.95% by weight. The content of 1-(4-chlorophenyl)-4,4-dimethyl-pentan-3-ol was 0.3% by weight and the content of 1-phenyl-4,4-dimethyl-pentan-3-one was 0.06% by weight. The content of 1-(4-chlorophenyl)-4,4-dimethyl-pentan-3-one was 99.24% by weight (remainder to 100%: starting material and unknown by-products).

After the distillative removal of the impurities, the 1-(4-chlorophenyl)-4,4-dimethyl-pentan-3-one isolated had a purity of 99.95% by weight.

Example 3

A vertical, thermally insulated high-pressure tube of stainless steel having an internal diameter of 45 mm and a length of 1 m was filled with 1.4 l of a hydrogenation catalyst produced by tableting powder of an Ni/Mo alloy having an Mo content of 1.75%, the catalyst having, at a cylinder height of 5 mm and a diameter of 5 mm, a compressive strength of 191N and an internal surface area of 58 m²/g. 1600 l/h of a 1-(4-chlorophenyl)-4,4-dimethyl-pent-1-en-3-one solution as in Example 1 were, together with the thirtyfold molar amount of high-purity hydrogen under a pressure of 300 bar, passed through this tube, namely from the bottom upwards.

Methanolic solution and hydrogen were brought to a temperature of 40° C. prior to entering into the high-pressure tube.

After a running time of 2800 hours, the conversion of the 1-(4-chlorophenyl)-4,4-dimethyl-pent-1-en-3-one used was 100% by weight. The content of 1-(4-chlorophenyl)-4,4-dimethyl-pentan-3-ol was 0.1% by weight and the content of 1-phenyl-4,4-dimethyl-pentan-3-one was 0.05% by weight. The content of 1-(4-chlorophenyl)-4,4-dimethyl-pentan-3-one was 99.45% by weight (remainder to 100%: unknown by-products).

Example 4

In a high-pressure tube as in Example 1 but made of high-pressure steel N 9, the same amount per hour of a 17% strength by weight solution of 1-(4-chlorophenyl)-4,4-dimethyl-pent-1-en-3-one in methanol was hydrogenated at a temperature of 45° C. and a hydrogen pressure of 300 bar. The catalyst was produced by tableting powder of an Ni/Mo alloy having an Mo content of 1.02% by weight and an Al content of 5.1% by weight. The tablets had, at a cylinder height of 5 mm and a diameter of 5 mm, a compressive strength of 210N and an internal surface area of 71 m²/g.

After a running time of 4200 hours, the conversion of the 1-(4-chlorophenyl)-4,4-dimethyl-pent-1-en-3-one used was 100% by weight. The content of 1-(4-chlorophenyl)-4,4-dimethyl-pentan-3-one in the solvent-free reaction eluate was 99.64% by weight. The content of 1-(4-chlorophenyl)-4,4-dimethyl-pentan-3-ol was 0.15% by weight and the content of 1-phenyl-4,4-dimethyl-pentan-3-one was 0.04% by weight (remainder to 100%: unknown by-products).

Example 5

In a high-pressure tube as in Example 1, the same amount per hour of a 17% strength by weight solution of 1-(4-chlorophenyl)-4,4-dimethyl-pent-1-en-3-one in methanol, additionally containing 0.1% by weight of NaOH and 0.2% by weight of bis-(2-hydroxy-ethyl)sulphide, was hydrogenated at a temperature of 60° C. and a hydrogen pressure of 300 bar. The catalyst was obtained by tableting Ni powder which additionally contained 5.8% by weight of Al. The tablets had, at a cylinder height of 3 mm and a diameter of 3 mm, a compressive strength of 168N and an internal surface area of 68 m²/g.

After a running time of 5300 hours, the conversion of the 1-(4-chlorophenyl)-4,4-dimethyl-pent-1-en-3-one used was 100% by weight. The content of 1-(4-chlorophenyl)-4,4-dimethyl-pentan-3-one in the solvent-free reaction eluate was 99.38% by weight. The content of 1-(4-chlorophenyl)-4,4-dimethyl-pentan-3-ol was 0.2% by weight and the content of 1-phenyl-4,4-dimethyl-pentan-3-one was 0.02% by weight (remainder to 100%: unknown by-products).

After the distillative removal of the impurities, the 1-(4-chlorophenyl)-4,4-dimethyl-pentan-3-one isolated had a purity of 99.9% by weight.

What is claimed is:

1. A process for the preparation of 1-(4-chlorophenyl)-4,4-dimethyl-pentane-3-one from 1-(4-chlorophenyl)-4,4-dimethyl-pent-1en-3-one which comprises hydrogenating continuously 1-(4-chlorophenyl)-4,4-dimethyl-pent-1-en-3-one in a solution of a monoalcohol with a 10-fold to 20-fold amount of hydrogen under a pressure of from 50 to 400 bar at a temperature of from 30° to 160° C. over a hydrogenation catalyst of support shaped bodies having a dimension of from 2 to 7 mm comprising (i) one or more elements of the iron subgroup of transistion group VIII of the Periodic Table, the shaped bodies being arranged in a fixed bed of a reactor having a compressive strength of from 20 to 250N on their surface and an internal surface area from 10 to 80 m$^2$/g.

2. The process of claim 1, in which the monoalcohol contains 1 to 4 carbon atoms.

3. The process of claim 1, in which the support-free bodies of (i) are additionally alloyed or mixed with (ii) elements of transition group VI which have an activating action.

4. The process of claim 1, in which the support-free bodies of (i) contain further (iii) one or more hydrogenation-inert element from the groups of aluminium, silicon, carbon and titanium.

5. The process of claim 1, in which the shaped bodies have a compressive strength of from 110 to 220N.

6. The process of claim 1, in which the shaped bodies, viewed macroscopically, have a smooth surface.

7. The process of claim 1, in which the shaped bodies are cylindrical and have a diameter of from 2 to 7 mm.

8. The process of claim 1, in which the shaped bodies are spherical and have a diameter of from 2 to 7 mm.

9. The process of claim 1, in which the hydrogenation temperature in the fixed-bed reactor is from 40° to 80° C.

10. The process of claim 1, in which a solution of 1-(4-chlorophenyl)-4,4-dimethyl-pent-1-en-3-one in methanol to be hydrogenated passes through the hydrogenation reactor from the bottom upwards.

11. The process of claim 1, in which the shaped bodies contain at least 60% by weight, based on the support-free shaped bodies, of metals (i).

12. The process of claim 1, in which the shaped bodies contain as (i) Ni in an amount of from 60 to 100% by weight.

13. The process of claim 3, in which the shaped bodies contain from zero to 15% by weight of metals (ii), based on the support-free shaped bodies.

14. The process of claim 4, in which the shaped bodies contain from zero to 25% by weight of elements (iii), based on the support-free shaped bodies.

* * * * *